United States Patent [19]
Giants et al.

[11] Patent Number: 4,720,590
[45] Date of Patent: Jan. 19, 1988

[54] [2,2,2-TRIHALO-1-(TRIHALOMETHYL)]E-
THYLIDENE-BISBENZENETHIOLS

[75] Inventors: Thomas W. Giants, Santa Monica; Thomas K. Dougherty, Rancho Palos Verdes, both of Calif.

[73] Assignee: Hughes Aircraft Company, Los Angeles, Calif.

[21] Appl. No.: 453,431

[22] Filed: Dec. 27, 1982

[51] Int. Cl.$^4$ ............... C07C 148/00; C07C 149/00
[52] U.S. Cl. ........................... 568/65; 568/56; 528/219; 528/374
[58] Field of Search ........................... 568/65

[56] References Cited

U.S. PATENT DOCUMENTS

| 3,274,267 | 9/1966 | Chow | 568/56 |
|---|---|---|---|
| 3,291,777 | 12/1966 | Stamatoff et al. | 528/9 |
| 3,332,909 | 7/1967 | Farnham et al. | 528/219 |
| 3,432,468 | 3/1969 | Gabler | 528/374 |
| 3,468,960 | 9/1969 | Mobbs | 568/65 |
| 3,736,293 | 5/1973 | Novak | 528/374 |
| 3,855,313 | 12/1974 | Metcalf et al. | 568/56 |
| 3,873,593 | 3/1975 | Heath et al. | 260/465 F |
| 3,929,852 | 12/1975 | Kydonieus et al. | 568/65 |
| 4,238,601 | 12/1980 | Keller et al. | 528/206 |

Primary Examiner—George F. Lesmes
Assistant Examiner—S. A. Gibson
Attorney, Agent, or Firm—M. E. Lachman; A. W. Karambelas

[57] ABSTRACT

[2,2,2-Trifluoro-1-(trifluoromethyl)]ethylidene-bisbenzenethiols are new compounds useful as precursors in the manufacture of polysulfide polymers and copolymers.

4 Claims, No Drawings

[2,2,2-TRIHALO-1-(TRIHALOMETHYL)]ETHYLIDENE-BISBENZENETHIOLS

BACKGROUND OF THE INVENTION

1. Field of the Invention

This invention relates to 2,2,2-(trihalomethyl)-1-ethylidenebisbenzenethiols which are precursors of polysulfide polymers and copolymers.

2. Description of the Prior Art

U.S. Pat. No. 3,929,852 shows, at Col. 5, substituted bisbenzenethiols linked by an alkylidene group, but without fluorine substituents on the linking alkyl group. U.S. Pat. Nos. 3,855,313; 3,274,267 and 3,468,960 disclose other bisphenols having alkyl thiol groups para to the bisphenol linkage, but none has the 2,2,2-trifluoro-1-trifluoromethyl-ethylidene linkage of our new compounds.

SUMMARY OF THE INVENTION

This invention provides a new class of bisbenzenethiols in which the linking group consists of a 2,2,2-trifluoro-1-(trifluoromethyl)ethylidene linkage. These new compounds are of the generic formula below:

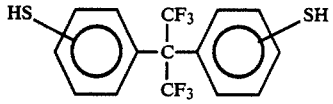

The thiol groups in the compounds of the generic formula above are positioned in either the meta or the para position.

DETAILED DESCRIPTION OF THE INVENTION

The process for making the bisbenzenethiols of the invention has three steps. In the first step, we react a bisphenol having the 2,2,2-trifluoro-1-(trifluoromethyl)ethylidene linkage with N,N-dimethylthiocarbamyl chloride in the presence of a base. Preferably, we use a 10% to 20% molar excess of the carbamyl chloride to bisphenol in this reaction. The preferred temperature range for the reaction is in the range of about 0° C. to about 60° C. at atmospheric pressure. The preferred time of reaction is in the range of about one to about two hours. From this first step of the process, we obtain a class of compounds called O-thiocarbamate esters.

In the second step of our process, we simply heat the O-thiocarbamate esters from the first step at a temperature in the range of about 250° C. to about 275° C. for a period in the range of about one to about two hours and at atmospheric pressure, preferably under an inert atmosphere such as argon, to form a class of compounds called S-thiocarbamate esters.

In the third step of our process, we treat the S-thiocarbamate esters from the second step with a strong base such as potassium hydroxide in methanol, and then treat with a concentrated acid such as hydrochloric or nitric to form the desired bisbenzenethiol.

The new bisbenzenethiols of this invention are useful as monomers in the formation of polysulfide polymers and copolymers. The hexafluoroisopropylidene group interrupts conjugation in such polymers, providing them with good tractability and maintaining good high performance properties.

The following examples illustrate the formation of the preferred bisbenzenethiol of this invention, namely 4,4'-[2,2,2-trifluoro-1-(trifluoromethyl)ethylidene]bisbenzenethiol.

To a solution containing 112 grams (0.33 mole) of bisphenol AF (4,4'-[2,2,2-trifluoro-2-(trifluoromethyl)ethylidene]bisphenol) and 700 milliliters of benzene we added 43.5 grams (0.66 mole) of 85% potassium hydroxide. We refluxed the resulting solution with a trap to remove water; then, we removed the benzene at reduced pressure. To the resulting salt we added 700 milliliters of dimethylformamide, cooled the mixture to 0° C., and then added 100 grams (0.81 mole) of N,N-dimethylthiocarbamyl chloride. We heated the resulting mixture to room temperature, then to 60° C., and maintained the mixture at 60° C. for one hour.

We diluted the product mixture with three liters of water and extracted the mixture twice with an 80:20 benzene/hexane solution. We evaporated the organic phase under reduced pressure and obtained a solid crystalline residue. We recrystallized the residue from a 5:1 methanol/benezene solution, and obtained 125 grams of a product melting at about 209°–211° C. We analyzed this product by NMR and elemental analysis, and found that the resulting product was the O-thiocarbamate ester of bisphenol AF [compound (1)]. We computed the resulting yield at 76% of the theoretically predicted amount.

We then placed 15 grams (0.3 mole) of compound (1) in a reaction vessel, and heated it at 250° C. under argon for one hour. After cooling the product to room temperature, we recrystallized the glassy residue from 60 milliliters of methanol, and obtained 11 grams of a product having a melting point of 141°–144° C. We analyzed this product by NMR and elemental analysis, and found that the resulting product was the S-thiocarbamate ester of the bisbenzenethiol derivative [compound (2)]. We computed the resulting yield as 75% of the empirically-predicted amount.

We then placed 75 grams (0.15 mole) of compound (2) in 400 milliliters of methanol, and added a solution of 75 grams of potassium hydroxide in 200 milliliters of water. We refluxed this mixture for one hour, cooled and diluted it with two liters of water. We then added a solution of 165 milliliters of concentrated HCl in one liter of water, and obtained a precipitate which we recrystallized from a 3:1 methanol-water mixture to obtain 50 grams (90% of the empirically-predicted amount) of a product having a melting point in the range of 112°–113° C. Upon analysis (NMR and elemental), we determined that the resulting product was 4,4'-[2,2,2-trifluoro-1-(trifluoromethyl)ethylidene]bisbenzenethiol.

We prepare the 3,3'-[2,2,2-trifluoro-1-(trifluoromethyl)ethylidene]bisbenzenethiol by a similar method. First, we dissolve 2,2-diphenylhexafluoropropane (138 grams, 0.455 mole) in 1.4 liters of dichloromethane. We add thereto 550 milliliters of concentrated sulfuric acid, and cool the resulting solution to 0° C. We then add fuming nitric acid (90% assay, 191 milliliters) dropwise to the solution over a period of 1.5 hours, maintaining the reaction temperature in the range of 0° C. to 6° C. and stirring well. We stir the mixture at ambient temperature for three hours, and transfer to a separatory funnel for removal of the aqueous phase. We then wash the organic phase three times with 500 milliliters of water and once with 500 milliliters of 15% sodium hydroxide in water. We continue the washing with 5% sodium hydroxide until the aqueous layer is colorless. We then wash the organic phase three times with 500 milliliters of water, dry over magnesium sulfate and concentrate to obtain 173 grams of a viscous yellow oil which solidifies upon trituration with methanol. Recrystallization of the resulting solid from 1.4 liters of absolute methanol, followed by two additional recrystallizations from methanol, gives analytically pure crystals of 2,2-bis(3-nitrophenyl)hexafluoropropane having a melting point of 118°–119° C.

We react this dinitro product with hydrogen gas under about 3 to about 4 atmosphere of pressure at ambient temperature and in the presence of a platinum catalyst, and obtain 2,2-bis(3-aminophenyl)hexafluoropropane. We then sublime this diamine under 5 microns of pressure, and recrystallize from heptane to obtain the desired product with a melting point of 84.5°–85.5° C. NMR, elemental and mass spectral (MS) analyses confirm this structure. Fourier-transform infrared spectroscopy reveals the absence of the para isomer.

To make the desired bisphenol from this diamine, we prepare a solution of 60 milliliters of concentrated hydrochloric acid, 200 milliliters of ice and 33.4 grams (0.1 mole) of 2,2-bis(3-aminophenyl)hexafluoropropane, and add thereto an aqueous solution of sodium nitrite (0.2 mole). We stir the mixture slowly, and heat to 80° C. for two hours. After the desired phenol separates, we extract it three times with 100 milliliters of ether each time, then wash the organic phase with water, sodium bicarbonate, and finally with saturated ammonium chloride. We then distill to obtain 33.6 grams of 2,2-bis(3-hydroxyphenyl)hexafluoropropane. From this bisphenol, we prepare the meta-substituted bisbenzenethiols of this invention following the same sequence of steps that produces the para-substituted bisbenzenethiols.

What is claimed is:

1. 2,2,2-Trifluoro-1-(trifluoromethyl)ethylidene-bisbenzenethiols of the following generic formula:

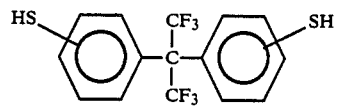

wherein the thiol groups are positioned meta or para to the ethylidene group.

2. The compound of claim 1 wherein the thiol groups are symmetrically positioned meta or para to the ethylidene group.

3. The compound of claim 2 wherein the compound is 4,4'-[2,2,2-trifluoro-1-(trifluoromethyl)ethylidene]bisbenzenethiol.

4. The compound of claim 2 wherein the compound is 3,3'-[2,2,2-trifluoro-1-(trifluoromethyl)ethylidene]bisbenzenethiol.

* * * * *